Figure 1:
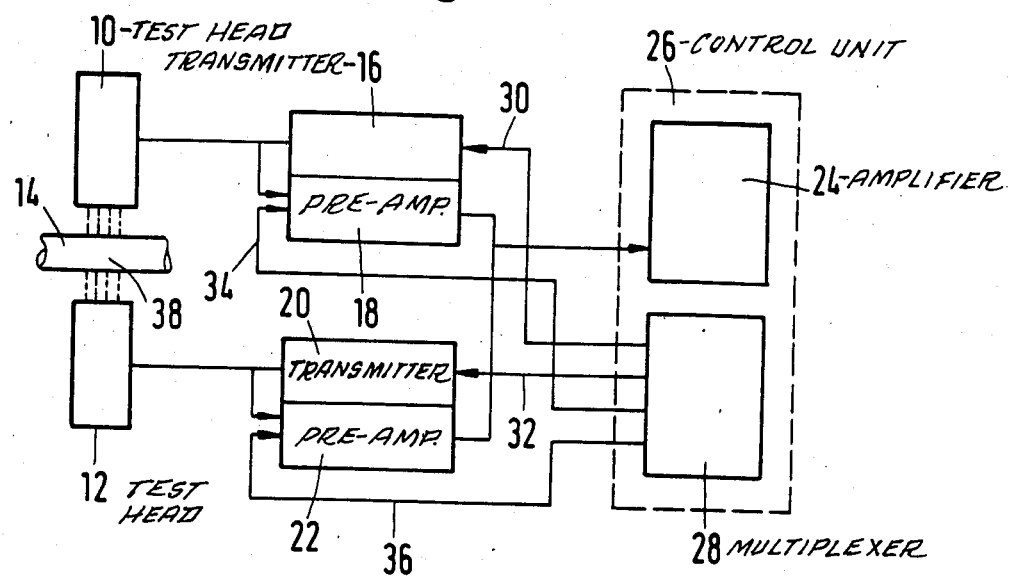

United States Patent [19]

Maurer

[11] Patent Number: 4,669,312

[45] Date of Patent: Jun. 2, 1987

[54] METHOD AND APPARATUS FOR ULTRASONIC TESTING OF DEFECTS

[75] Inventor: Albrecht Maurer, Seligenstadt, Fed. Rep. of Germany

[73] Assignee: Nukem Gmbh, Hanau am Main, Fed. Rep. of Germany

[21] Appl. No.: 729,146

[22] Filed: Apr. 30, 1985

[30] Foreign Application Priority Data

May 5, 1984 [DE] Fed. Rep. of Germany ....... 3416709

[51] Int. Cl.$^4$ ............................................. G01N 29/00
[52] U.S. Cl. ......................................... 73/600; 73/599
[58] Field of Search ................................. 73/599, 600

Primary Examiner—Howard A. Birmiel
Attorney, Agent, or Firm—Cushman, Darby & Cushman

[57] ABSTRACT

The object of the invention is a method for the non-destructive testing of workpieces (14) or components with ultrasonics and a device for applying the method. The workpieces (14) are subjected in accordance with the through-transmission principle at the same locations (38) in succession with ultrasonic waves that differ by their opposing directions under conditions that are otherwise the same. The ultrasonic signals received in the two different sound directions are, provided they have different signal amplitudes, compared with given values obtained from a similar workpiece with defects in previously known depth in order to determine the depth of defect in the workpiece (14). If the sound absorption is complete, the ultrasonic waves continue to be applied in opposite directions to neighboring positions until ultrasonic signals are received whose differences are evaluated in order to determine the depth of the defect concerned.

6 Claims, 3 Drawing Figures

METHOD AND APPARATUS FOR ULTRASONIC TESTING OF DEFECTS

The invention relates to a method and apparatus for testing workpieces and components (e.g., test specimens) with ultrasonics, where the test speciment is examined by ultrasonic waves penetrating the specimen from opposed sides, e.g. the through-transmission method.

In the past, the ultrasonic pulse echo method was generally used for the non-destructive detection of internal defects in workpieces because the depth of the defect could also be detected by this method thus allowing accurate defect assessment by the DGS or test sample method. In the pulse echo method, the object to be tested need be accessible from one side only, in contrast to the through-transmission method. The pulse echo method cannot be applied, however, if defects close to the surface are to be detected because these defect indications disappear in the echo from the front or back surface, or if very high absorption or scatter make detection impossible of the ultrasonic echo that has passed twice through the object to be tested.

The through-transmission method is used in the cases where the sound pressure amplitude of the ultrasonic wave generated by the transmitter test head in the material is measured by the receiver test head on the opposite side of the workpiece.

If there is a defect in the material, the sound wave generated by the transmitter is shadowed by the defect and the receiving test head receives the signals in weakened form.

It can therefore be concluded that there is a defect in the material as a result of the attenuation of the ultrasonic signal detected in the receiver test head. Since there is no delay signal, however, that can be associated with the defect signal, it is not possible to say anything about the depth of the defect and thus no assessment of the defect can be made.

The German patent application No. 26 04 651 describes a method of the type mentioned at the outset that is combined with the pulse echo method. In the German patent application No. 16 48 341 a method is described for determining the depth of surfaces reflected by ultrasonics in a body, where the pulse echo method and the through-transmission method are applied.

The invention is based on the requirements of making available a method for non-destructive testing of workpieces or components with ultrasonics on the through-transmission principle and a device for applying the method that also allows the depth of defects to be evaluated.

In accordance with the present invention, defects can be detected even when the dimensions of the defects are greater than the diameter of the transmitter and receiver test heads. In the case of defects whose dimensions are smaller than the diameter of the transmitter test head or of the ultrasonic bundle, a physical property of sound fields is used, in which, after the shadowing by an obstacle as represented by a material defect, a homogenous sound field again exists at a certain distance away from the obstacle.

This means that the amplitude of the measured sound pressure under an obstacle depends for equal obstacle sizes on the distance between obstacle and receiver test head, and again approximates the sound pressure amplitude in the undisturbed case as the distance increases. Test head parameters that also have an influence on the test results must be kept constant during measurement.

Whereas defects located centrally in the test piece lead to equal amplitude signals in the receiver in both test directions, off-center defects in the specimen generate different amplitude signals in the two representative specimen. Using a suitable test sample, defects are analysed at different depths by this same method and a calibration curve is plotted that establishes a unique relationship between the values of the amplitude signals in different test directions and at different depths of the defect. The calibration curve is used in testing specimens having unknown defects by comparing the amplitude of measured sound pressure of the specimen with the amplitudes given in the calibration curve.

If the magnitude of the relevant defect exceeds the diameter of the transmitter test head or of the ultrasonic wave bundle used for measurement, ultrasonic absorption occurs that exists in both directions. This case can be determined by the output signals of the receiver. In order to measure the depth of the defect, the measuring point on the specimen is moved away by a certain amount until the ultrasonic wave bundle no longer completely encounters the point of the defect. Ultrasonic waves then still arrive at the receiver that depend on the position of the edge of the defect and on the depth of the defect. The location of the defect edge does not change with the different directions of the ultrasonic waves. The differences in amplitude of sound pressure that result for the different directions of the ultrasonic waves can therefore be used for establishing the depth of the defect.

A particular advantage of the method described herein is that a mean value can be formed from the values obtained from the measurements in two different test directions and on which changes in intensity due to the direction of motion have no influence. Furthermore, strength-influencing defects in or near the skin of the specimen can be advantageously differentiated from defects located at the center that have no influence on the strength of the specimen as a whole. The places in the specimen containing defects can thus be reworked when the depth of the defect is specified.

A device with two test heads arranged at the same distance from the surface on opposite sides of the specimen and coupled to them in the same way, where the receivers are connected to a main amplifier in order to implement the test method include transmitters and receivers being alternately activatable for the two test heads by a multiplexer that can be operated from a central control unit.

Figure 2:
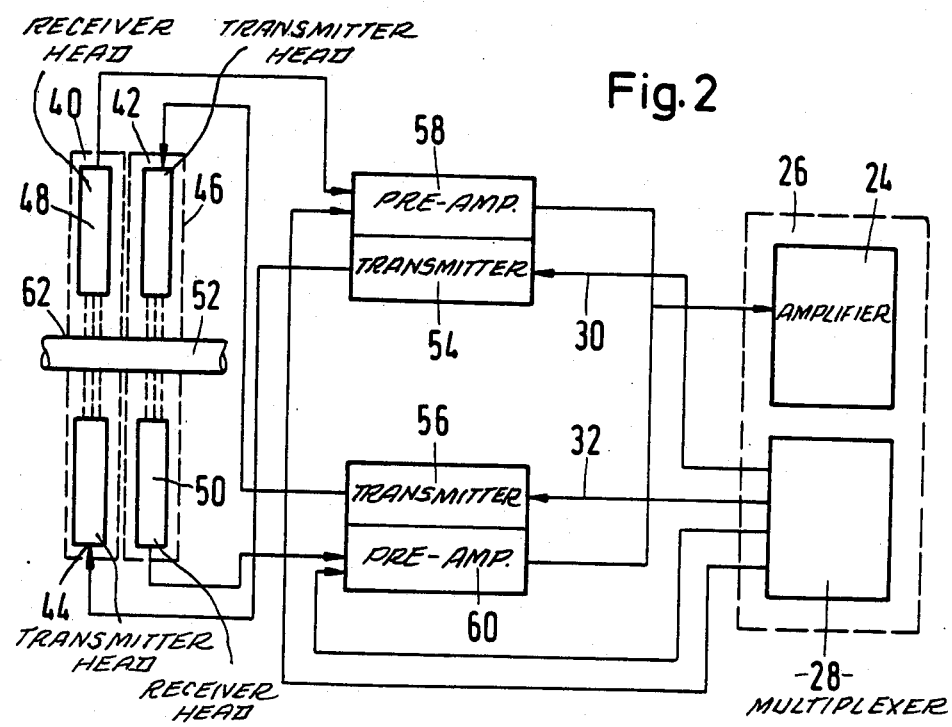
Figure 3:
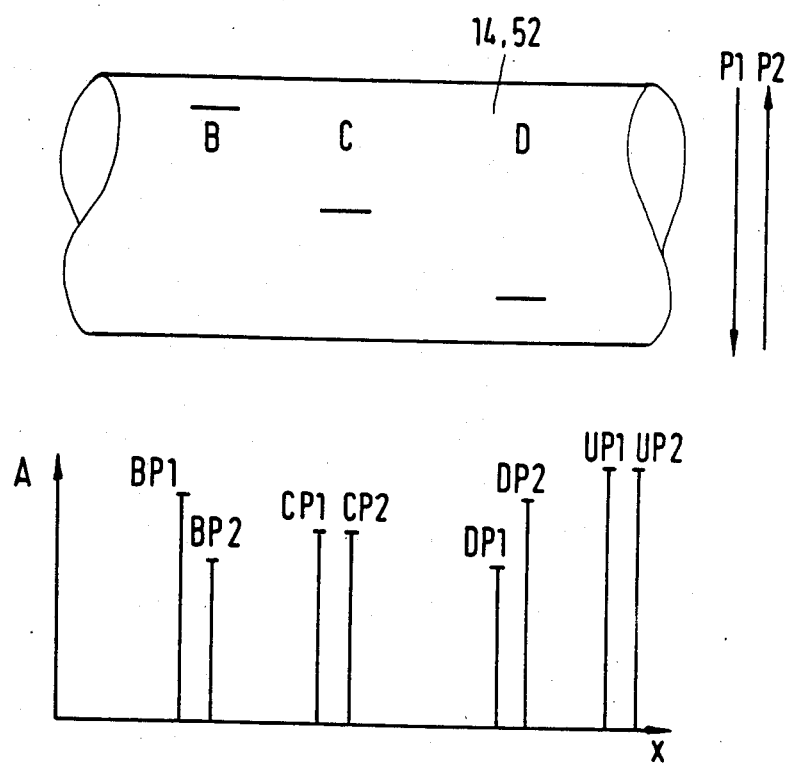

Further details, advantages and characteristics of the invention are given not only in the claims but also in the following description of the drawing, in which;

FIG. 1 is a block diagram of a first arrangement for testing specimens with ultrasonics by the through-transmission principle, FIG. 2 is a block diagram of a second arrangement for testing specimen with ultrasonics by the through-transmission principle, and FIG. 3 is a schematic representation of amplitudes related to the defects that exist in a specimen.

Two ultrasonic test heads 10, 12 are arranged on two opposite sides of a specimen 14 that may be, for example, a piece of sheet metal. The two ultrasonic test heads 10, 12 are of identical construction. The ultrasonic test heads are also arranged at the same distance from the surface of the workpiece and coupled to the associated surface, for example, directly or through a water lead section. The ultrasonic test head 10 is connected with a transmitter 16 for high frequency electrical signals and with a preamplifier 18. Similarly, the ultrasonic test head 12 is connected with a transmitter 20 which also generates high frequency electrical signals and with a preamplifier 22. The frequency of the high frequency electrical signals is in the ultrasonic range. Both ultrasonic test heads 10, 12 can be operated both as ultrasonic transmitters and as ultrasonic receivers.

The outputs of the preamplifiers 18, 22 are connected with the input of a main amplifier 24 that is located in a central control unit 26. The control unit 26 also contains a multiplexer 28 that is connected with the transmitters 16, 20 through lines 30, 32 respectively and with the preamplifiers 18, 22 through lines 34, 36 respectively.

The multiplexer 28 issues a first control signal at successive time intervals of uniform length onto line 30 in order to activate transmitter 16 and a second control signal on line 32 in order to activate transmitter 20. These signals are also known as "triggers". While the control signal is on line 30, the multiplexer 28 activates the preamplifier 22 through line 36. When a control signal is applied to line 32, the multiplexer 28 activates the preamplifier 18 through line 34. Thus the ultrasonic test heads 10, 12 are operated alternately as transmitters and receivers and connected with the transmitters 16, 20 or with the preamplifiers 18,22. The control signals for activating the preamplifiers 18, 22 are also known as "gates".

During two successive test cycles, the specimen 14 remains in the same position, i.e. in specimen 14 the same position 38 shown with dotted lines in FIG. 1 is tested with ultrasonic waves that travel in opposite directions. The amplitude signal of sound pressure measured at the same position 38 during two successive test operations are supplied through the main amplifier 24 to an evaluation unit that is not described in detail in which they are compared with previously stored values that are stored preferably in the form of a curve or table. The curve or table specifies the magnitudes of sound pressure amplitudes as a function of the depth of defects in the inside of the specimen for a like specimen that corresponds in shape and dimensions. The curve is obtained be means of a test sample method.

The principle of this method is that one or several specimens containing defects at known depths are measured using the device shown in FIG. 1. The sound pressure amplitudes found at these depths are measured. The measured values are found in accordance with the known error depths from the curve or table described above. The evaluation obtained for specimens 14 is performed by comparing the measured values with this curve in the control unit 26. The curve serves to determine the depth of defects whose dimensions are smaller than the diameter of the ultrasonic test head 10, 12 or smaller than the diameter of the ultrasonic wave bundle in specimen 14. If the dimensions in the table are greater than the aforementioned diameter, then sound absorption takes place. This can be established on the basis of the output signals of the ultrasonic test head 10,12 that operate as receivers. In this case the measurement is performed at another place adjacent to the place at which the sound absorption occurs. After sound absorption has been established, either the specimen or the ultrasonic test head 10, 12 is moved by a certain amount while the measurements described above are repeated.

The measurements are continued at new adjacent points in a scanned manner until no further sound absorption takes place. The difference between the received ultrasonic waves that pass through the edge of the respective defect point in opposite directions is then used in order to determine the depth of the defect.

The above-mentioned curve specifies preferably the ratio of the sound pressure amplitudes established in the two different directions of through-transmission on test samples in relation to the depth of defect. It thus always involves the mean values of the sound pressure amplitudes. By establishing the mean values, influences that are related to the period of operation and which could adulterate the measuring results are eliminated. The outline diagram in FIG. 3 shows how the sound pressure amplitudes vary according to the defect depth and test direction. For test directions $P_1$ and $P_2$ the sound pressure amplitudes $BP_1$, $BP_2$, $CP_1$, $CP_2$, $DP_1$, $DP_2$ vary in relation to the defect location B, C, D. If no defect is found, the sound pressure amplitudes $UP_1$ and $UP_2$ are obtained. The comparison between these sound pressure amplitudes and those that are found in the center of the specimen 14, 52 when a defect C exists shows that the latter are less even if no differences are found with respect to test direction $P_1$, $P_2$. The difference between the same amplitudes $CP_1$, $CP_2$ and $UP_1$, $UP_2$ respectively does however show that there is a defect in the center of the workpiece 14, 52.

In the embodiment shown in FIG. 2, there are two pairs of transmitters/receivers 40, 42 for ultrasonic waves. Each pair of transmitters/receivers 40, 42 has its own transmitter test head 44 and 46 and receiver test head 48 and 50 respectively. The transmitter/receiver test heads 44, 48 and 46, 50 respectively are arranged to the two opposite sides of a specimen 52 that is to be tested such that the directions of the ultrasonic waves are opposed to each other. Furthermore, the transmitter/receiver test heads 44, 48 and 46, 50 respectively are of the same design in each transmitter/receiver pair 40, 42. The transmitter/receiver test heads 44, 48 and 46, 50 respectively are also coupled in the same way to the surface of the specimen 52.

The transmitter test heads 44, 46 are connected with the transmitters 54, 56 respectively. Preamplifiers 58, 60 are connected to the transmitter test heads 48, 50 respectively. The preamplifiers 58, 60 are connected with their outputs to the main amplifier 24 in the control unit 26. The multiplexer 28 is connected through line 30, 32 with transmitters 54, 56 and through line 34, 36 with preamplifiers 58, 60 respectively.

For the through-transmission test, the specimen 52 is subjected to ultrasonic waves with mutually opposing directions in succession at the same point 62 as shown with dotted lines in FIG. 2 with the transmitter/receiver pairs 40, 42. The transmitter/receiver pairs 40, 42 are therefore arranged in the same test track with respect to the direction of motion of specimen 52. It is also possible to keep the specimen 52 in one particular location and to move the transmitter/receiver pairs during the test.

The examination of specimen 52 at location 62 is performed in such a way that first of all the transmitter 54 is activated through line 30 and the preamplifier 58 through line 34. After this, the specimen 52 for example is pushed forward until the transmitter/receiver test pair is located opposite to location 62. Subsequently the transmitter 56 is activated through line 32 and the preamplifier 60 through line 36. The two transmitter/- receiver pairs can be kept continuously in operation if, for example, two separate main amplifiers are used and which are followed by memories from which the measured values can be called at any time.

The sound pressure amplitudes established in the two measuring cycles are evaluated for determination of depths of defects in the manner described above with respect to the arrangement shown in FIG. 1. The calibration with specified test samples of equal shape and dimensions as specimen 62 is performed with the arrangement shown in FIG. 2.

The curves obtained by the test sample method are contained preferably in digital form in a memory belonging to control unit 26. Control unit 26 has advantageously a microprocessor that puts the two sound pressure amplitudes measured in successive test cycles into relation with each other and compares the quotients thus obtained with the curve. The comparison establishes whether there is a defect in the material and whether the defect is in the center of the material or away from the center. If the defect is away from the center, the curve specifies the depth of the defect. The half in which the defect is located is obtained from the sequence of the measured sound pressure amplitudes.

The foregoing description of the illustrative embodiments may be modified by those skilled in the art in accordance with the above teachings. Accordingly, it is the intent of the applicant to incllude all such modifications and varations as may come to those skilled in the art. The scope of the invention, however, is pointed out with particularity by the appended claims.

What is claimed to be secured by U.S. Letters Patent is:

1. A method for non-destructive testing of defects in a speciment comprising the steps of:
   directing first and second ultrasonic waves through the specimen from opposed sides thereof at scanned locations about a defect,
   detecting at each scanned location said first and second ultrasonic waves after passage through said specimen,
   comparing respective energy levels of said first and second detected ultrasonic waves with reference levels generated by testing a representative specimen having a defect of a known depth, and
   generating information characteristic of said defect in said specimen as a result of said comparison.

2. An apparatus for non-destructive testing of defects in a specimen comprising:
   transmitting means for directing first and second ultrasonic waves through the specimen from opposed sides thereof at selected locations,
   receiving means for detecting said first and second ultrasonic waves after passage thereof through said specimen at said selected locations,
   means for comparing the respective energy levels of said first and second detected ultrasonic waves with reference levels generated by testing a representative specimen having a known defect, and
   means for generating defect information characteristic of said defect as a result of said comparison.

3. An apparatus as recited in claim 2 further including amplifier means for amplifying signals received from said receiving means, said transmitting means and said receiving means comprising a pair of transmitters and a pair of receivers, and further including multiplexer means for alternately enabling a selected transmitter and receiver, and for alternately coupling said enabled receiver to said amplifier means thereby to generate said defect information.

4. An apparatus as recited in claim 2 further including amplifier means for amplifying signals received from said receiving means, said transmitting means and said receiving means comprising opposed ultrasonic transceivers located on opposite sides of the specimen, and further including multiplexer means for alternately enabling a selected portion of said transceivers and for alternately coupling an enabled receiver portion of said transceiver to said amplifier means thereby to generate said defect information.

5. An apparatus as recited in claim 4 wherein said amplifier means comprises an amplifier and a preamplifier.

6. An apparatus as recited in claim 3 wherein said amplifier means comprises an amplifier and a preamplifier.

* * * * *